United States Patent [19]

Pamukcu et al.

[11] Patent Number: 5,852,035
[45] Date of Patent: Dec. 22, 1998

[54] METHOD FOR INHIBITING NEOPLASTIC CELLS AND RELATED CONDITIONS BY EXPOSURE TO SUBSTITUTED N-ARYLMETHYL AND HETEROCYCLMETHYL-1H-PYRAZOLO (3, 4-B) QUINOLIN-4-AMINES

[75] Inventors: Rifat Pamukcu, Spring House; Gary A. Piazza, Doylestown, both of Pa.

[73] Assignee: Cell Pathways, Inc., Horsham, Pa.

[21] Appl. No.: 989,357

[22] Filed: Dec. 12, 1997

[51] Int. Cl.⁶ .................... A61K 31/44; A61K 31/535
[52] U.S. Cl. ........................ 514/293; 514/236.5
[58] Field of Search ................ 514/293, 236.5

[56] References Cited

U.S. PATENT DOCUMENTS

| | | | |
|---|---|---|---|
| 3,031,450 | 4/1962 | Fischer et al. | 260/247.5 |
| 3,161,654 | 12/1964 | Shen | 260/319 |
| 3,322,755 | 5/1967 | Roch et al. | 260/246 |
| 3,517,005 | 6/1970 | Cronin et al. | 260/256.4 |
| 3,594,480 | 7/1971 | Cronin et al. | 424/250 |
| 3,647,858 | 3/1972 | Hinkley et al. | 260/470 |
| 3,654,349 | 4/1972 | Shen et al. | 260/615 M |
| 3,780,040 | 12/1973 | Schnettler et al. | 260/256.5 |
| 3,812,127 | 5/1974 | Cronin et al. | 260/268 BQ |
| 3,819,631 | 6/1974 | Broughton et al. | 260/256.4 F |
| 3,920,636 | 11/1975 | Takahasi et al. | 260/240 J |
| 4,001,237 | 1/1977 | Partyka et al. | 424/251 |
| 4,001,238 | 1/1977 | Partyka et al. | 424/251 |
| 4,039,544 | 8/1977 | Broughton et al. | 260/256.4 F |
| 4,060,615 | 11/1977 | Matier et al. | 424/251 |
| 4,079,057 | 3/1978 | Juby et al. | 424/251 |
| 4,098,788 | 7/1978 | Crenshaw et al. | 544/293 |
| 4,101,548 | 7/1978 | Crenshaw et al. | 544/284 |
| 4,102,885 | 7/1978 | Crenshaw et al. | 544/286 |
| 4,138,561 | 2/1979 | Crenshaw et al. | 544/284 |
| 4,146,718 | 3/1979 | Jenks et al. | 544/292 |
| 4,161,595 | 7/1979 | Kaplan et al. | 544/284 |
| 4,171,363 | 10/1979 | Crenshaw et al. | 424/251 |
| 4,208,521 | 6/1980 | Crenshaw et al. | 544/250 |
| 4,209,623 | 6/1980 | Juby | 544/319 |
| 4,423,075 | 12/1983 | Dvornik et al. | 424/317 |
| 4,460,590 | 7/1984 | Möller | 424/251 |
| 4,460,591 | 7/1984 | DeGraw et al. | 424/251 |
| 4,880,810 | 11/1989 | Lowe, III et al. | 514/258 |
| 4,885,301 | 12/1989 | Coates | 514/263 |
| 4,923,874 | 5/1990 | McMahon et al. | 514/258 |
| 5,073,559 | 12/1991 | Coates | 514/262 |
| 5,147,875 | 9/1992 | Coates et al. | 514/259 |
| 5,223,501 | 6/1993 | Chakravarty et al. | 514/258 |
| 5,250,535 | 10/1993 | Verheyden et al. | 514/262 |
| 5,254,571 | 10/1993 | Coates et al. | 514/340 |
| 5,358,952 | 10/1994 | Moschel et al. | 514/262 |
| 5,401,774 | 3/1995 | Pamukcu et al. | 514/569 |
| 5,439,895 | 8/1995 | Lee et al. | 514/63 |
| 5,614,530 | 3/1997 | Kumar et al. | 514/293 |
| 5,614,627 | 3/1997 | Takase et al. | 544/293 |

FOREIGN PATENT DOCUMENTS

| | | |
|---|---|---|
| 0 347146 A2 | 12/1989 | European Pat. Off. . |
| 0 349239 A2 | 1/1990 | European Pat. Off. . |
| 0 351058 | 1/1990 | European Pat. Off. . |
| 0 352960 A2 | 1/1990 | European Pat. Off. . |
| 0 395328 A2 | 10/1990 | European Pat. Off. . |
| 0 428268 A2 | 5/1991 | European Pat. Off. . |
| 0 463756 A1 | 1/1992 | European Pat. Off. . |
| 0 485157 A2 | 5/1992 | European Pat. Off. . |
| 0 485158 A2 | 5/1992 | European Pat. Off. . |
| 0 485171 A2 | 5/1992 | European Pat. Off. . |
| 0 485172 A2 | 5/1992 | European Pat. Off. . |
| 0 485173 A2 | 5/1992 | European Pat. Off. . |
| 0 508586 A1 | 10/1992 | European Pat. Off. . |
| 0 526004 A1 | 2/1993 | European Pat. Off. . |
| 0 607439 A1 | 7/1994 | European Pat. Off. . |
| 3038166 | 5/1981 | Germany . |
| 56-53659 A | 5/1981 | Japan . |
| 57-167974 A | 10/1982 | Japan . |
| 807826 | 1/1959 | United Kingdom . |
| 2063249 | 6/1981 | United Kingdom . |
| WO 92/03419 | 3/1992 | WIPO . |
| WO 93/07149 | 4/1993 | WIPO . |
| WO 93/12095 | 6/1993 | WIPO . |
| WO 94/05661 | 3/1994 | WIPO . |
| WO 97/03985 | 2/1997 | WIPO . |

OTHER PUBLICATIONS

Waddell, W.R. et al., Am. J. Surgery, vol. 157, pp. 175–179 (1989).
Gonzaga, R.A.F. et al., The Lancet, Mar. 30, 1985, p. 751.
Waddell, W.R. et al., J. Surg. Oncology. vol. 24, pp. 83–87 (1983).
Federation Proceedings (1972) of the Federation of American Societies for Experimental Biology abstract Nos. 2044 and 2045.
Gilman, S.C. et al., Nonsteroidal Anti–inflammatory Drugs in Cancer Therapy, (circa 1985).
Brogden, R.N. et al., Drugs, vol. 16, pp. 97–114 (1978).
Hucker, H.B. et al., Drug Metabolism & Disposition, vol. 1, No. 6, pp. 721–736 (1973).
Shen, T.Y. et al., Chemical and Biological Studies on Indomethacin, Sulindac and Their Analogs, pp. 107–178 (circa 1975).
Duggan, D.E. et al., Clin. Pharm. & Therapeutics,. vol. 21, No. 3, pp. 326–335 (1976).
Duggan, D.E. et al., J. Pharm. & Exper. Therap., vol. 201, No. 1, pp. 8–13 (1977).
Glavin, G.B. et al., Toxicology and Applied Pharmacology, vol. 83, pp. 386–389 (1986).
Moorghen, M. et al., Journal of Pathology, vol. 156, pp. 341–347 (1988).
Moorghen, M. et al.,Acta Histochemica, Suppl.–Band XXIX, S. 195–199 (1990).
Bjarnason et al., Gastroenterology, vol. 94, No. 4, pp. 1070–1074 (1988).

(List continued on next page.)

*Primary Examiner*—Jerome D. Goldberg
*Attorney, Agent, or Firm*—Robert W. Stevenson

[57] ABSTRACT

A method for inhibiting neoplastic cells and related conditions by exposing them to substituted N-arylmethyl and heterocyclmethyl-1H-pyrazolo[3,4-B]quinolin-4-amines.

15 Claims, No Drawings

OTHER PUBLICATIONS

Badrieh, Y., et al., Chem. Ber., vol. 125, pp. 667–674 (1992).

Silvola, J. et al., Effects of nonsteroidal anti–inflammatory drugs on rat gastric mucosal phosphodiesterase activity, Agents and Actions, vol. 12.4, pp. 516–520 (1982).

Curtis–Prior, P.B. et Cyclic Nucleotide Phosphodiesterase Activity of Human Normal and Carcinomatous Lung Tissue, The Lancet, pp. 1225–1225 Dec. 4, 1976.

Pepin, P. et al., Effects of Sulindac and Oltipraz on the tumorigenicity of 4–(methylnitrosamino) 1–(3–pyridyl)–1–Butanone in A/J mouse lung, Carcinogenesis, vol. 13, No. 3, pp. 341–348 (1992).

Nicholson, C.D. et al. Differential modulation of tissue function and therapeutic potential of selective inhibitors of cyclic nucleotide phosphodiesterase isoenzymes,Trends Pharmacol. Sci. (TiPS), vol. 12, pp. 19–27 (1991).

Ahn, H.S. et al., Effects of Selective Inhibitors on Cyclic Nucleotide Phosphodiesterases of Rabbit Aorta, Biochemical Pharmacology, vol. 38, No. 19, pp. 3331–3339 (1989).

Luginer, C. et al., Selective Inhibition of cyclic Nucleotide Phosphodiesterases of Human, Bovine and Rat Aorta, Biochem, Pharmacology, vol. 35, No. 10, pp. 1743–1751 (1986).

Turner, N.C. et al., Relaxation of guinea–pig trachea by cyclic AMP phosphodiesterase inhibitors and their enhancement by sodium mitroprusside, Br. J. Pharmacol. vol. III, pp. 1047–1052 (1994).

Weishaar, R.E. et al., Multiple Molecular Forms of Cyclic Bucleotide Phosphodiesterase in Cardiac and Smooth Muscle and In Platelets, Biochem. Pharmacology, vol. 35, No. 5, pp. 787–800 (1986).

Murray, K.J. et al., Potential Use of Selective Phosphodiesterase Inhibitors in the Treatment of Asthma, New Drugs for Asthma Therapy, Birkhauser Verlag Basel, pp. 27–46 (1991).

Saeki, T. et al., Isolation of Cyclic Nucleotide Phosphodiesterase Isozymes From Pig Aorta, Biochem. Pharmacology, vol. 46, No. 5, pp. 833–839 (1993).

Turner, N.C. et al., Pulmonary effects of type V cyclic GMP specific phosphodiesterase inhibition in anaesthetized guniea–pig, Br. J. Pharmacol., vol. 111, 1198–1204 (1994).

Ferreira, S.H. et al., The molecular mechanism of action of peripheral morphone analgesia: stimulation of the cGMP system via nitric oxide release, European Journal of Pharmacology, 201 pp. 121–122 (1991).

Hidaka, H. et al., Selective Inhibitors of Three Forms of cyclic Nucleotide Phosphodiesterase—Basic and Potential Clinical Applications, vol. 16, Advances in Cyclic Nucleotide and Protein Phosphorylation Research, pp. 245–259 (1984).

Tulshian, D. et al., Synthesis and Phosphodiesterase Activity of Carboxylic Acid Mimetics of Cyclic Guanosine 3",5"–Monophosphate, J. Med. Chem. vol. 36, 1210–1220 (1993).

Yasumoto, T. et al., Properties of Base–Substituted and Carboxyl–Esterified Analogues of Griseolic Acid, a Potent cAMP Phosphodiesterase Inhibitor, Biochemical Pharmacology, vol. 43, No. 10, pp. 2073,2081 (1992).

Broughton, B.J. et al., Antiallergic Activity of 2–Phenyl–8–azapruin–6–ones, Journal of Medicinal Chemistry, vol. 18, No. 11, pp. 1117–1118 (1975).

Kodama, K. et al., Effects of a novel, selective and potent phosphodiesterase type V inhibitor, E4021, on myocardial ischemia in guinea pigs, Euro. J. of Pharma. 263, pp. 93–99 (1994).

Zacharski, L. R. et al., Effect of Mopidamol on Survival in Carcinoma of the Lung and Colon: Final Report of Veterans Administration Cooperative Study No. 188, J. of the Nat'l. Cancer Inst., vol. 80, No. 2, pp. 90–96 (1988).

Lichtner, R. B. et al., The Pyrimido–pyrimidine Derivatives RA 233 adn RX–RA 85 affect Growth and Cytoskeletal Organization of Rat Mammary Adenocarcinoma Cells, Eur. J. Cancer Clin. Oncol., vol. 23, No. 9, pp. 1269–1275 (1987).

Janik, P. et al., Inhibition of Growth of Primary and Metastatic Lewis Lung carcinoma Cells by the Phosphodiesterase Inhibitor Isobutylmethylxanthine, Cancer Res. vol. 40, pp. 1950–1954, (Jun. 1980).

Bergstrand, Hakan et al., Effects of Antiallergic Agents, Compound 48/80, and Some Reference Inhibitors on the Activity of Partially Purified Human Lung Tissue Adenosine Cyclic 3',5'–Monophosphate and Guanposine Cyclic 3',5'–Monophosphate Phosphodiesterases. Molecular Pharmacology, 13, pp. 38–43 (1976).

Drees, Markus et al., 3',5'–Cyclic Nucleotide Phosphodiesterase in Tumor Cells as Potential Target for Tumor Growth Inhibition, Cancer Research 53, pp. 3058–3061 (1993).

Semmler, J. et al., Xanthine derivaties: comparison between suppression of tumor necrosis factor–x production and inhibition of cAMP phosphodiesterase activity, Immunology 78, pp. 520–525 (1993).

Mehta, Rajendra et al., Structure–Activity Relationships of Brassinin in Preventing the Development of Carcinogen–Induced Mammary Lesions in Organ Culture, Anticancer Research 14: 1209–1214 (1994).

Makaryan, A.P. et al., Cyclic Nucleotides in Patients with Malignant Neoplasms of the Colon, Laboratornoe Delo, vol. 8, pp. 31–33 (1991).

Carter et al., Chemotherapy of Cancer, $2^{nd}$ Ed., John Wiley & Sons, NY, NY, 1981, pp. 362–365.

Biddle, William et al., Antineoplastic Effect of the Pyrimido–Pyrimidine Derivative: RA 233, Pathologie Biologie, Jan., 1984, pp. 9–13.

Clarke, W.R. et al., The type III phosphodiesterase inhibitor milrinone and type V PDE inhibitor dipyridamole individually and synergistically reduce elevated pulmonary vascular resistance Abstract Only, Pulum. Pharmacol., 7(2), pp. 81–89, (1984).

Raeburn, David et al., Effects of isoenzyme–selective inhibitors of cyclic nucleotide phosphodiesterase on microvascular leak in guinea pig airways in vivo (Abstract Only), J. Pharmacol. Exp. Ther., 267(3), pp. 1147–1151 (1993).

Marcoz, P. et al., Modulation of rat thymocyte proliferative response through the inhibition of different cyclic nucleotide phosphodiesterase isoforms by means of selective inhibitors and CGMP–elevating agents (Abstract Only), Mol. Pharmacol. 44(5) pp. 1027–1035 (1993).

Barnett, Mary S. et al., Initial biochemical and functional characterization of cyclic nucleotide phosphodiesterase isozymes in canine colonic smooth muscle (Abstract Only), J. Pharmacol. Exp. Ther., 264(2) pp. 801–812 (1993).

Molnar–Kimber, K. et al., Modulation of TNFa and IL–1B from indotoxin–stimulated monocytes by selective PDE isozyme inhibitors (Abstract Only), Agents Actions 39(Spec. Conf. Issue), C77–C79 (1993).

Giorgi, Mauro et al., Characterization of 3':5' cyclic nucleotide phosphodiesterase activities of mouse neuroblastoma N18TG2 cells (Abstract Only), FEBS Lett. 324(1) pp. 76–80 (1993).

Porter, Roderick et al., Preparation of 6–phenyl–3–(5–tetrazoly)pyridin–2(H)–one derivatives as cyclic AMP–dependent protein kinase agonists (Abstract Only), PCT Int. Appl. WO9206085 A1, (Sep. 26, 1991).

Molnar–Kimber, K.L. et al., Differential regulation of TNF–a and IL–1B production from endotoxin stimulated human monocytes by phosphodiesterase inhibitors (Abstract Only), Mediators Inflammation 1(6) pp. 411–417 (1992).

Radomski, Marek W. et al., Human Colorectal adenocarcinoma cells; differential nitric oxide synthesis determines their ability of aggregate platelets (Abstract Only), Cancer Res. 51(22) pp. 6073–6078 (1991).

Anderson, Thomas L. G. et al., Interactions between isoprenaline, sodium nitroprusside, and isozyme–selective phosphodiesterase inhibitors on ADP–induced aggretation and cyclic Nuycleotide levels in human platelets (Abstract Only), J. Cardiovasc. Pharmacol. 18(2) pp. 237–242 (1991).

Souness, John E. et al., Role of Selective cyclic GMP phosphodiesterase inhibition in the myorelaxant actions of M&B 22,943, MY–5445, vinpocetine and 1–methyl–3–isobutyl–8–(methylamino)xanthine (Abstract Only), Br. J. Pharmacol. 98(3) pp. 725–734 (1989).

Lichtner, Rosemarie B., The pyrimidopyrimidine derivatives RA233 and RX–RA85 affect cell cycle distribution of two murine tumor cell lines (Abstract Only), Eur. J. Cancer Clin. Oncol. 25(6), pp. 945–951 (1989).

Mamytbekova, A., et al., Antimetastatic effect of flurbiprofen and other platelet aggregation inhibitors (Abstract Only), Neoplasma 33(4), pp. 417–421 (1986).

Hagiwara, Masatoshi et al., Effect of 1–(3–chloroanilino)–4–phenylpthalazine (MY–5445), a specific inhibitor of cyclic CMP phosphodiesterase, on human platelet aggregation (Abstract Only), J. Pharmacol. Exp. Ther. 229(2) pp. 467–471 (1984).

METHOD FOR INHIBITING NEOPLASTIC CELLS AND RELATED CONDITIONS BY EXPOSURE TO SUBSTITUTED N-ARYLMETHYL AND HETEROCYCLMETHYL-1H-PYRAZOLO (3, 4-B) QUINOLIN-4-AMINES

TECHNICAL FIELD

This invention relates to a method for the selective inhibition of neoplastic cells, for example, for the treatment or prevention of precancerous lesions or other neoplasias in mammals.

BACKGROUND OF THE INVENTION

Each year in the United States alone, untold numbers of people develop precancerous lesions, which is a form of neoplasia, as discussed below. Such lesions exhibit a strong tendency to develop into malignant tumors, or cancer. Such lesions include lesions of the breast (that can develop into breast cancer), lesions of the skin (that can develop into malignant melanoma or basal cell carcinoma), colonic adenomatous polyps (that can develop into colon cancer), and other such neoplasms. Compounds that prevent or induce the remission of existing precancerous or cancerous lesions or carcinomas would greatly reduce illness and death from cancer.

For example, approximately 60,000 people die from colon cancer, and over 150,000 new cases of colon cancer are diagnosed each year. For the American population as a whole, individuals have a six percent lifetime risk of developing colon cancer, making it the second most prevalent form of cancer in the country. Colon cancer is also prevalent in Western Europe. It is believed that increased dietary fat consumption is increasing the risk of colon cancer in Japan.

In addition, the incidence of colon cancer reportedly increases with age, particularly after the age of 40. Since the mean ages of populations in America and Western Europe are increasing, the prevalence of colorectal cancer should increase in the future.

To date, little progress has been made in the prevention and treatment of colorectal cancer, as reflected by the lack of change in the five-year survival rate over the last few decades. The only cure for this cancer is surgery at an extremely early stage. Unfortunately, most of these cancers are discovered too late for surgical cure. In many cases, the patient does not experience symptoms until the cancer has progressed to a malignant stage.

In view of these grim statistics, efforts in recent years have concentrated on colon cancer prevention. Colon cancer usually arises from pre-existing benign neoplastic growths known as polyps. Prevention efforts have emphasized the identification and removal of colonic polyps. Polyps are identified by x-ray and/or colonoscopy, and usually removed by devices associated with the colonoscope. The increased use of colon x-rays and colonoscopies in recent years has detected clinically significant precancerous polyps in four to six times the number of individuals per year that acquire colon cancer. During the past five years alone, an estimated 3.5 to 5.5 million people in the United States have been diagnosed with adenomatous colonic polyps, and it is estimated that many more people have or are susceptible to developing this condition, but are as yet undiagnosed. In fact, there are estimates that 10–12 percent of people over the age of 40 will form clinically significant adenomatous polyps.

Removal of polyps has been accomplished either with surgery or fiber-optic endoscopic polypectomy—procedures that are uncomfortable, costly (the cost of a single polypectomy ranges between $1,000 and $1,500 for endoscopic treatment and more for surgery), and involve a small but significant risk of colon perforation. Overall, about $2.5 billion is spent annually in the United States in colon cancer treatment and prevention.

In the breast, breast cancer is often treated surgically, often by radical mastectomy with its painful aftermath. Such surgery is costly, too.

As indicated above, each lesion carries with it a chance that it will develop into a cancer. The likelihood of cancer is diminished if a precancerous lesion is removed. However, many of these patients demonstrate a propensity for developing additional lesions in the future. They must, therefore, be monitored periodically for the rest of their lives for reoccurrence.

In most cases (i.e. the cases of sporadic lesion formation, e.g. so-called common sporadic polyps), lesion removal will be effective to reduce the risk of cancer. In a small percentage of cases (i.e. cases where numerous lesions form, e.g. the so-called polyposis syndromes), removal of all or part of the effected area (e.g. the colon) is indicated. For example, the difference between common sporadic polyps and polyposis syndromes is dramatic. Common sporadic polyp cases are characterized by relatively few polyps which can usually be removed leaving the colon intact. By contrast, polyposis syndrome cases can be characterized by many (e.g. hundreds or more) of polyps—literally covering the colon in some cases—making safe removal of the polyps impossible short of surgical removal of the colon.

Because each lesion carries with it a palpable risk of cancerous development, patients who form many lesions (e.g. polyposis syndrome patients) invariably develop cancer if left untreated. Surgical removal of the colon is the conventional treatment in polyposis patients. Many polyposis patients have undergone a severe change in lifestyle as a result of the disfiguring surgery. Patients have strict dietary restrictions, and many must wear ostomy appliances to collect their intestinal wastes.

The search for drugs useful for treating and preventing cancer is intensive. Indeed, much of the focus of cancer research today is on the prevention of cancer because chemotherapy for cancer itself is often not effective and has severe side effects. Cancer chemoprevention is important for recovered cancer patients who retain a risk of cancer reoccurrence. Also, cancer prevention is important for people who have not yet had cancer, but have hereditary factors that place them at risk of developing cancer. With the development of new genetic screening technologies, it is easier to identify those patients with high-risk genetic factors, such as the potential for polyposis syndrome, who would greatly benefit from chemopreventative drugs. Therefore, finding such anti-cancer drugs that can be used for prolonged preventive use is of vital interest.

Known chemopreventative and chemotherapeutic drugs are believed to kill cancer cells by inducing apoptosis, or as sometimes referred to as "programmed cell death." Apoptosis naturally occurs in virtually all tissues of the body, and especially in self-renewing tissues such as bone marrow, gut, and skin. Apoptosis plays a critical role in tissue homeostasis, that is, it ensures that the number of new cells produced are correspondingly offset by an equal number of cells that die. For example, the cells in the intestinal lining divide so rapidly that the body must eliminate cells after only three days in order to prevent the overgrowth of the intestinal lining.

Recently, scientists have realized that abnormalities of apoptosis can lead to the formation of precancerous lesions and carcinomas. Also, recent research indicates that defects in apoptosis play a major role in other diseases in addition to cancer. Consequently, compounds that modulate apoptosis could be used to prevent or control cancer, as well as used in the treatment of other diseases.

Unfortunately, even though known chemotherapeutic drugs may exhibit such desirable apoptosis effects, most chemotherapeutic drugs have serious side effects that prohibit their long-term use, or use in otherwise healthy individuals with precancerous lesions. These side effects, which are a result of the high levels of cytotoxicity of the drugs, include hair loss, weight loss, vomiting, immune suppression and other toxicities. Therefore, there is a need to identify new drug candidates for therapy that do not have such serious side effects in humans.

In recent years, several non-steroidal anti-inflammatory drugs ("NSAIDs"), originally developed to treat arthritis, have shown effectiveness in inhibiting and eliminating colonic polyps. Polyps virtually disappear when the patients take the drug, particularly when the NSAID sulindac is administered. However, the prophylactic use of currently available NSAIDs, even in polyposis syndrome patients, is marked by severe side reactions that include gastrointestinal irritations and ulcerations. Once NSAID treatment is terminated due to such complications, the polyps return, particularly in polyposis syndrome patients.

Sulindac has been particularly well received among the NSAIDs for the polyp treatment. Sulindac is a sulfoxide compound that itself is believed to be inactive as an antiarthritic agent. The sulfoxide is reportedly converted by liver enzymes to the corresponding sulfide, which is acknowledged to be the active moiety as a prostaglandin synthesis inhibitor. The sulfide, however, is associated with the side effects of conventional NSAIDs. The sulfoxide is also known to be metabolized to sulfone compound that has been found to be inactive as an inhibitor of prostaglandin synthesis but active as an inhibitor of precancerous lesions.

SUMMARY OF THE INVENTION

This invention includes a method of inhibiting neoplastic cells by exposing those cells to a pharmacologically effective amount of those compounds described below. Such compounds are effective in modulating apoptosis and eliminating and inhibiting the growth of neoplasias such as precancerous lesions, but are not characterized by the severe side reactions of conventional NSAIDs or conventional chemotherapeutics.

The compounds of that are useful in the methods of this invention include those of Formula I:

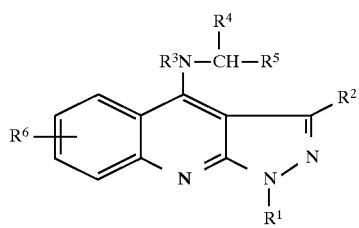

wherein:
$R_1$ is lower-alkyl;
$R_2$ is hydrogen, or lower-alkyl;
$R_3$ is hydrogen, or lower-alkyl;
$R_4$ is hydrogen, or lower-alkyl;
$R_5$ is phenyl (or phenyl substituted by from one to three, the same or different, substituents selected from the group consisting of lower-alkoxy, cyano, hydroxy, 4-morpholinylloweralkoxy, lower-alkyl, and halogen), phenyl-lower-alkyl, pyridinyl, furanyl, isoxazolyl, thienyl, oxazolyl, thiazolyl, pyridazinyl, pyrazinyl, and pyrimidinyl; or $R_4$ and $R_5$ together with the CH group to which they are bonded form an indanyl ring; and
$R_6$ is from one to three, the same or different, substituents selected from the group consisting of hydrogen, lower-alkoxy, hydroxy, lower-alkyl, and halogen; or a pharmaceutically acceptable acid-addition salt and/or hydrate thereof, or, where applicable, enantiomer or a racemic mixture.

DETAILED DESCRIPTION OF THE INVENTION

As discussed above, this invention is a method of inhibiting neoplastic cells by exposing them to compounds of formula I above.

Preferred compounds useful in the methods of this invention are those of Formula I above wherein:
$R_1$, $R_2$ and $R_3$ are as defined above;
$R_4$ is hydrogen;
$R_5$ is phenyl (or phenyl substituted by from one to two, the same or different, substituents selected from the group consisting of lower-alkoxy, cyano, hydroxy, and 4-morpholinyllower-alkoxy), phenyl-lower-alkyl, pyridinyl, or furanyl; or $R_4$ and $R_5$ together with the CH group to which they are bonded form an indanyl ring; and
$R_6$ is one substituent selected from the group consisting of hydrogen, lower-alkoxy, and hydroxy.

Particularly preferred compounds of Formula I above are those wherein:
$R_1$ is methyl, ethyl, or isopropyl;
$R_2$ is hydrogen, or methyl;
$R_3$ is hydrogen, or methyl;
$R_4$ is hydrogen;
$R_5$ is phenyl (or phenyl substituted by from one to two, the same or different, substituents selected from the group consisting of lower-alkoxy, cyano, hydroxy, and 4-morpholinyllower-alkoxy), phenyl-lower-alkyl, pyridinyl, or furanyl; or $R_4$ and $R_5$ together with the CH group to which they are bonded form an indanyl ring; and
$R_6$ is one substituent selected from the group consisting of hydrogen, methoxy, and hydroxy.

The most preferred compounds of the Formula I above are those wherein:
$R_1$, $R_2$, $R_3$, $R_4$ and $R_6$ are as defined as "particularly preferred compounds" above;
and
$R_5$ is phenyl (or phenyl substituted by from one to two, the same or different, substituents selected from the group consisting of methoxy, cyano, hydroxy, and 2-(4-morpholinyl)ethoxy), benzyl, 2-, 3-, 4-pyridinyl, or 2-furanyl; or $R_4$ and $R_5$ together with the CH group to which they are bonded form an indanyl ring. Examples of most preferred compounds useful in this invention are N-(phenylmethyl)-1-ethyl-1H-pyrazolo[3,4-b]quinolin-4-amine; N-(2-furanylmethyl)-1-ethyl-1H-pyrazolo[3,4-b]quinolin-4-amine; and N-(4-methoxyphenylmethyl)-1-ethyl-6-methoxy-1H-pyrazolo [3,4-b]quinolin-4-amine.

The term "lower-alkyl" as used herein means linear or branched hydrocarbon chains having from one to about five carbon atoms (e.g., ethyl, propyl, isopropyl, n-butyl, sec-butyl, and the like).

The term lower-alkoxy as used herein means linear or branched alkyloxy substituents having from one to about four carbon atoms and thus includes methoxy, ethoxy, propoxy, isopropoxy, butoxy, sec-butoxy, and the like.

The term halogen, halide, or halo as used herein means bromine, chlorine, iodine or fluorine.

Preferably, such compounds are administered without therapeutic amounts of an NSAID.

The present invention is also a method of treating mammals with precancerous lesions by administering a pharmacologically effective amount of an pharmaceutical composition (preferably enterically coated) that includes compounds of Formula I.

In still another form, the invention is a method of inducing apoptosis in human cells by exposing those cells to an effective amount of compounds of formula I, wherein $R_1$ through $R_6$ to those cells sensitive to such a compound.

As used herein, the term "precancerous lesion" includes syndromes represented by abnormal neoplastic, including dysplastic, changes of tissue. Examples include adenomatous growths in colonic, breast or lung tissues, or conditions such as dysplastic nevus syndrome, a precursor to malignant melanoma of the skin. Examples also include, in addition to dysplastic nevus syndromes, polyposis syndromes, colonic polyps, precancerous lesions of the cervix (i.e., cervical dysplasia), prostatic dysplasia, bronchial dysplasia, breast, bladder and/or skin and related conditions (e.g., actinic keratosis), whether the lesions are clinically identifiable or not.

As used herein, the term "carcinomas" refers to lesions that are cancerous. Examples include malignant melanomas, breast cancer, and colon cancer.

As used herein, the term "neoplasm" refers to both precancerous and cancerous lesions as well as hyperplastic conditions.

Compounds useful in the methods of this invention may be formulated into compositions together with pharmaceutically acceptable carriers for oral administration in solid or liquid form, or for rectal or topical administration, although carriers for oral administration are most preferred.

Pharmaceutically acceptable carriers for oral administration include capsules, tablets, pills, powders, troches and granules. In such solid dosage forms, the carrier can comprise at least one inert diluent such as sucrose, lactose or starch. Such carriers can also comprise, as is normal practice, additional substances other than diluents, e.g., lubricating agents such as magnesium stearate. In the case of capsules, tablets, troches and pills, the carriers may also comprise buffering agents. Carriers such as tablets, pills and granules can be prepared with enteric coatings on the surfaces of the tablets, pills or granules. Alternatively, the enterically coated compound can be pressed into a tablet, pill, or granule, and the tablet, pill or granules for administration to the patient. Preferred enteric coatings include those that dissolve or disintegrate at colonic pH such as shellac or Eudraget S.

Pharmaceutically acceptable carriers include liquid dosage forms for oral administration, e.g. pharmaceutically acceptable emulsions, solutions, suspensions, syrups and elixirs containing inert diluents commonly used in the art, such as water. Besides such inert diluents, compositions can also include adjuvants such as wetting agents, emulsifying and suspending agents, and sweetening, flavoring and perfuming agents.

Pharmaceutically acceptable carriers for rectal administration are preferably suppositories that may contain, in addition to the compounds of Formula I, excipients such as cocoa butter or a suppository wax.

The pharmaceutically acceptable carrier and compounds of this invention are formulated into unit dosage forms for administration to a patient. The dosage levels of active ingredient (i.e. compounds of this invention) in the unit dosage may be varied so as to obtain an amount of active ingredient effective to achieve lesion-eliminating activity in accordance with the desired method of administration (i.e., oral or rectal). The selected dosage level therefore depends upon the nature of the active compound administered, the route of administration, the desired duration of treatment, and other factors. If desired, the unit dosage may be such that the daily requirement for active compound is in one dose, or divided among multiple doses for administration, e.g., two to four times per day.

The pharmaceutical compositions of this invention are preferably packaged in a container (e.g. a box or bottle, or both) with suitable printed material (e.g. a package insert) containing indications, directions for use, etc.

The synthesis of compounds useful in practicing this invention is described in U.S. Pat. No. 5,614,530 as shown in the following Scheme A:

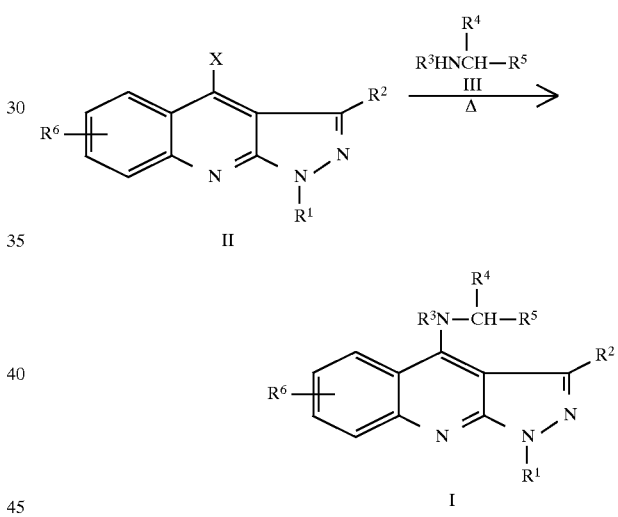

A suitably substituted 4-halo-1H-pyrazolo[3,4-b] quinoline of the formula II, wherein X is a halogen, preferably chlorine, in a suitable organic solvent, such as dimethylsulfoxide, is treated with at least one mole of a suitably substituted amine of the formula III, at a temperature in the range of about room temperature up to the boiling point of the solvent used, preferably at a temperature in the range of about 80° C. up to the boiling point of the solvent used, to afford the substituted 1H-pyrazolo[3,4-b]quinolin-4-amines of the formula I.

Simple chemical transformations which are conventional and well known to those skilled in the art of chemistry can be used for effecting changes in the functional groups of the compounds of the formula I. For example, the dealkylation of aryl ether derivatives to afford the corresponding phenol derivatives.

It will be appreciated that compounds of Formula I can possess an asymmetric carbon atom and are thus capable of existing as enantiomers. Unless otherwise specified herein, the practice of this invention is intended to extend to each of the enantiomeric forms, including the racemates. In some cases there may be advantages, i.e. greater potency, to using one enantiomer over another enantiomer or the racemate in the methods of the instant invention and such advantages can be readily determined by those skilled in the art. The separate enantiomers may be synthesized from chiral starting materials, or the racemates may be resolved by conventional procedures which are well known in the art of chemistry such as chiral chromatography, fractional crystallization of diastereomeric salts, and the like.

Compounds of Formula I are useful both in the free base form and in the form of acid-addition salts, and, both forms are within the purview of the invention. The acid-addition salts are often a more convenient form for use; and in practice, use of the salt form inherently amounts to use of the base form. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial properties inherent in the free base are not vitiated by side effects ascribable to the anions. In making compounds useful in this invention, it is convenient to use the free base form or the hydrochloride, fumarate, toluenesulfonate, methanesulfonate or maleate salts.

However, other appropriate pharmaceutically acceptable salts within the scope of the invention are those derived from other mineral acids and organic acids. The acid-addition salts of the basic compounds are prepared by standard procedures well known in the art which include, but are not limited thereto, dissolving the free base in an aqueous alcohol solution containing the appropriate acid and isolating the salt by evaporating the solution, or by reacting the free base and an acid in an organic solvent, in which case the salt separates directly, or is precipitated with a second organic solvent, or can be obtained by concentration of the solution. Although medicinally acceptable salts of the basic compounds are preferred, all acid-addition salts are within the scope of the present invention. All acid-addition salts are useful as sources of the free base form even if the particular salt per se is desired only as an intermediate product, as, for example, when the salt is formed for purposes of purification or identification, or when it is used as an intermediate in preparing a medicinally acceptable salt by, for example, ion exchange procedures.

The suitably substituted 4-halo-1H-pyrazolo[3,4-b]quinolines of Formula II, which are required for the synthesis of the compounds of Formula I, can be prepared as shown in Scheme B:

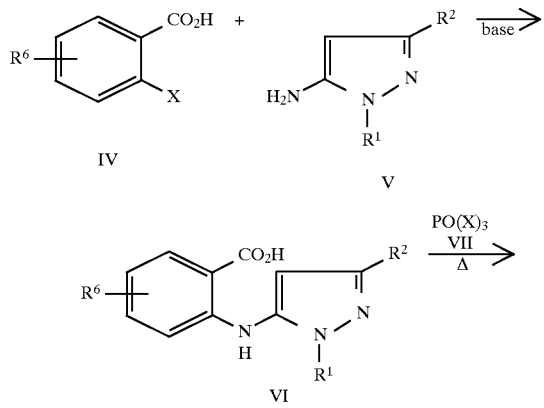

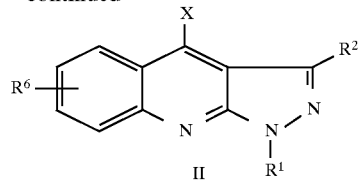

A suitably substituted benzoic acid derivative of the formula IV, wherein X is a halogen, preferably iodine, or bromine, in a suitable organic solvent, such as dimethylformamide, is treated with at least one mole of a suitable base, such as potassium carbonate, at least one mole of a suitably substituted pyrazole derivative of Formula V and a catalytic amount of Cu(OAc)2 or copper, at a temperature in the range of about room temperature up to the boiling point of the solvent used, preferably at the boiling point of the solvent used, to afford the suitably substituted anthranilic acid derivatives of Formula VI. The suitably substituted anthranilic acid derivative of the formula VI can then be treated with an excess of a phosporous oxyhalide of the Formula VII, wherein X is a halogen, preferably chlorine, at a temperature in the range of about room temperature up to the boiling point of the reaction mixture, preferably at a temperature in the range of about 90° C. up to the boiling point of the reaction mixture, to afford the compounds of the Formula II.

The suitably substituted amines of Formula III, the suitably substituted benzoic acid derivatives of Formula IV and the suitably substituted pyrazole derivatives of Formula V are either commercially available, or they can be prepared by procedures known in the art, or by the procedures described in the examples below.

The structures of the compounds of the invention reportedly are established by the mode of synthesis, and by one or more of elemental analysis, and infrared, nuclear magnetic resonance and mass spectroscopy. The course of the reactions and the identity and homogenity of the products are reportedly assessed by one or more of thin layer chromatography (TLC), high pressure liquid chromatography (HPLC), or gas-liquid chromatography (GLC).

The following examples from the aforesaid U.S. patent will further illustrate compounds useful in practicing the methods of this invention without, however, limiting it thereto. All melting points (m.p.) are given in degrees centigrade (°C.) and are uncorrected.

EXAMPLES

Example 1

(a) A mixture of 1-ethyl-4-chloro-1H-pyrazolo[3,4-b]quinoline (15.0 g, 0.065 mol), benzylamine (15.6 ml, 0.14 mol) and DMSO (100 ml) is heated at 80° C. overnight. The reaction mixture is poured into ice/water and the gummy solid which formed is collected by filtration. The solid is dissolved in ethyl acetate, dried over MgSO4, filtered and concentrated. The residual oil is crystallized from ethyl acetate to afford 18 g (92%) of 1-ethyl-N-(phenyl methyl)-1H-pyrazolo[3,4-b]quinolin-4-amine, m.p. 130°–132° C.

(b) 1-Ethyl-N-(phenylmethyl)-1H-pyrazolo[3,4-b]quinolin-4-amine (1.0 g) is dissolved in warm methanol and is treated with an equimolar amount of methanesulfonic acid. The mixture is cooled in an ice-bath, then ether is added and the resulting solid is collected by filtration and recrystallized from isopropanol to afford 0.84 g of 1-ethyl-N-(phenylmethyl)-1H-pyrazolo[3,4-b]quinolin-4-amine.CH3SO3H, as a white solid, m.p. 255°–257° C.

Example 2

(a) To 2-iodobenzoic (250 g, 1.01 mol) in DMF (2 L) is added K2CO3 (154.8 g, 1.12 mol), then 5-amino-1-ethylpyrazole (112.3 g, 1.01 mol) and finally copper (II) acetate monohydrate (4.2 g, 0.021 mol). The reaction mixture is refluxed overnight and then the DMF is removed under reduced pressure. The residue is poured into ice water (2 L), and the mixture is acidified with acetic acid to a pH of about 5–6. A precipitate forms which is collected by filtration, washed with water and dried in vacuo at 60°–70° C. to afford 278 g of N-(1-ethylpyrazol-5-yl)anthranilic acid.

(b) A mixture of N-(1-ethylpyrazol-5-yl)anthranilic acid (278 g, 1.2 mol) and POCl3 (550 g, 3.6 mol) is refluxed for 3 hours. The reaction mixture is cooled and then poured into ice/water (3–4 L). A solid forms which is collected by filtration and washed with water. The filtrate is extracted with CH2Cl2 (1 L) and the CH2Cl2 layer is evaporated to about 50 ml, and both this solution and the previously isolated solid are purified by colunm chromatography on silica gel eluting with CH2Cl2 to afford 190 g (68%) of 1-ethyl-4-chloro-1H-pyrazolo[3,4-b]quinoline.

(c) A mixture of 1-ethyl-4-chloro-1H-pyrazolo[3,4-b] quinoline (11.6 g, 0.05 mol), DMSO (20 ml) and phenethylamine (12.1 g, 0.1 mol) is heated at 80° C. overnight. The reaction mixture is poured into water (1 L), and the precipitate that forms is collected by filtration and washed with water. The solid is dissolved in hot ethyl acetate, and then the solution is dried over MgSO4, filtered and evaporated to a small volume. Hexane is added, and then the mixture is cooled in an ice bath, and then the product that crystallizes is collected by filtration, washed with hexane and dried to afford 12.5 g of 1-ethyl-N-(phenylethyl)-1H-pyrazolo[3,4-b]quinoline-4 amine, m.p. 157°–158° C.

Example 3

A mixture of 1-ethyl-4-chloro-1H-pyrazolo[3,4-b] quinoline (10 g, 0.043 mol), 4-methoxybenzylamine (13.0 g, 0.095 mol) and DMSO (75 ml) is heated at reflux overnight and then is allowed to stand for about 2 days. The reaction mixture is poured into ice water, and the resulting gum is treated with ethyl acetate. The product that oils out of the ethyl acetate is separated and then is dissolved in CH2Cl2. The CH2Cl2 layer is washed with water, then brine and then is dried over MgSO$_4$ and evaporated under reduced pressure. The residue is dissolved in CH2Cl2 and purified by column chromatography on silica gel eluting with CH2Cl2 to afford the product as the free base. The free base is dissolved in methanol, and then is treated with methanolic HCl. A precipitate forms which is collected by filtration, washed with ether and dried in vacuo at 50° C. to afford 12.4 g of 1-ethyl-N-(4-methoxy phenylmethyl)-1H-pyrazolo[3,4-b] quinolin-4-amine.HCl.½ H2O, m.p. 179°–180° C.

Example 4

(a) To 2-iodobenzoic acid (54 g, 0.218 mol) in DMF (570 ml) is added K2CO3 (33.4 g, 0.242 mol), then 5-amino-1-isopropylpyrazole (27.3 g, 0.218 mol) and finally copper (II) acetate monohydrate (0.9 g, 4.5 mmol). The reaction mixture is refluxed overnight and then the DMF is evaporated. The residue is poured into ice/water and then the mixture is acidified with acetic acid and concentrated HCl to a pH of about 4. A precipitate forms which is collected by filtration, washed with water and dried in a vacuum oven at 40° C. to afford 52 g (97.2%) of N-(1-isopropylpyrazol-5-yl) anthranilic acid.

(b) A mixture of N-(1-isopropylpyrazol-5-yl) anthranilic acid (52 g, 0.212 mol) and POCl3 (436 ml, 4.68 mol) is refluxed for 3 hours, then is stirred at room temperature overnight. The excess POCl$_3$ is removed by distillation and then the residue is poured into ice/water. The mixture is neutralized with 35% NaOH and then extracted with CH2Cl2. The CH2Cl2 layer is separated and washed with water, then brine and then is dried over MgSO4, filtered and evaporated. The residue is dissolved in CH2Cl2 and then is purified by column chromatography on silca gel eluting with CH2Cl2 to afford 21.3 g (40.9%) of 1-isopropyl-4-chloro-1H-pyrazolo[3,4-b]quinoline.

(c) To a solution of 1-isopropyl-4-chloro-1H-pyrazolo[3,4-b]quinoline (10.6 g, 0.043 mol) in dimethylsulfoxide (75 ml) is added benzylamine (10.2 g, 0.095 mol). The reaction mixture is refluxed for 4.5 hours and then is allowed to stand at room temperature overnight. The reaction mixture is poured into ice/water and the precipitate that formed is collected by filtration and dissolved in CH2Cl2. The CH2Cl2 layer is washed with brine, dried over MgSO4 and then evaporated in vacuo. The residue is dissolved in CH2Cl2 and purified by column chromatography on silca gel to afford, after recrystallization from hexane, 1-isopropyl-N-(phenylmethyl)-1H-pyrazolo[3,4-b]quinolin-4-amine, m.p. 162°–164° C.

Example 5

(a) 2-Nitro-4-methoxybenzoic acid (43.4 g, 0.22 mol) in DMF (250 ml) is hydrogenated at 55 psi in the presence of 10% palladium on carbon (5.8 g) for 2.5 hours. The reaction mixture is filtered through SUPERCELL™, the filter cake is rinsed with ethanol, and then the filtrate is poured into ice water (3.5 L). A precipitate forms which is collected by filtration, washed with water and dried in an oven at 60° C. to afford 30.7 g (84%) of 4-methoxyanthranilic acid, m.p. 176°–178° C. (dec.).

(b) A mixture of 4-methoxyanthranilic acid (30.5 g, 0.18 mol), water (274.5 ml), and concentrated HCl (36.6 ml) is heated at 75° C. to effect solution and then is cooled to 0° C. The mixture is then treated with NaNO2 (13.3 g) in water (27.5 ml), followed by potassium iodide (45.75 g) in a water (75 ml)/H2SO4 (10.1 ml) solution. The reaction mixture is heated on a steam bath for 2 hours, then excess iodine is steam distilled. The reaction mixture is then cooled, and the product is collected by filtration and dried in an oven at 75° C. to afford 39.28 g (78.6%) of crude product. The crude product is treated with toluene, the mixture is filtered, and the filtrate is concentrated to afford 26.03 g of 2-iodo-4-methoxybenzoic acid.

(c) K2CO3 (13.94 g, 0.101 mol) is dissolved in water (67 ml), and then 2-iodo-4-methoxybenzoic acid (25.3 g, 0.091 mol) is added, followed by 5-amino-1-ethylpyrazole (11.2 g, 0.101 mol) and finally copper (2.7 g). The reaction mixture is refluxed for 20 hours, cooled to room temperature. Then water (350 ml) is added, and the mixture is refluxed for 0.75 hours. The reaction mixture is cooled, and the product is collected by filtration, recrystallized from ethanol, and dried in an oven at 40° C. to afford 13.37 g (56%) of N-(1-ethylpyrazol-5-yl)-4-methoxyanthranilic acid, m.p. 130°–135° C.

(d) A mixture of N-(1-ethylpyrazol-5-yl)-4-methoxyanthranilic acid (13.3 g, 0.051 mol) and POCl3 (125 ml) is refluxed for 3 hours, then is allowed to sit overnight. The volume of POCl3 is reduced, then ice water, followed by NH4OH are added. A precipitate forms which is collected by filtration and dried in a vacuum oven at 50°

C. to afford 11.51 g (87%) of 1-ethyl-4-chloro-7-methoxy-1H-pyrazolo[3,4-b]quinoline, m.p. 95°–98° C.

(e) A mixture of 1-ethyl-4-chloro-7-methoxy-1H-pyrazolo[3,4-b]quinoline (11.5 g, 0.044 mol), DMSO (70 ml) and benzylamine (10.56 ml, 0.095 mol) is heated on a steam bath for 18 hours. The reaction mixture is added to ice water, and a solid formed which is collected by filtration, washed with water and dissolved in ethyl acetate. The ethyl acetate layer is dried over MgSO4, filtered and evaporated. The residue is taken up in ether (500 ml), filtered and concentrated to afford 11.7 g of the product which is recrystallized from ether to afford 9.35 g of 1-ethyl-7-methoxy-N-(phenylmethyl)-1H-pyrazolo[3,4-b]quinolin-4-amine, m.p. 163°–164.5° C.

Example 6

1-Ethyl-7-methoxy-N-(phenylmethyl)-1H-pyrazolo[3,4-b]quinolin-4-amine (4 g, 0.012 mol) in DMF (70 ml) is treated with 60% NaH (2.4 g, 0.06 mol), followed by butane thiol (5.4 g, 0.06 mol). The reaction mixture is refluxed overnight and then is poured into ice water. The mixture is acidified with 2N HCl and then is extracted with ethyl acetate (2×500 ml). The aqueous layer is treated with solid NaHCO3 to adjust the pH to about 8, then the mixture is extracted with ethyl acetate (2×500 ml). The ethyl acetate layers are combined, washed with water, filtered and evaporated. The solid residue is recrystallized from ethyl acetate (2×) to afford 1.44 g of 1-ethyl-7-hydroxy-N-(phenylmethyl)-1H-pyrazolo[3,4-b]quinolin-4-amine, m.p. 252°–254° C.

Example 7

A mixture of 1-ethyl-4-chloro-1H-pyrazolo[3,4-b]quinoline (1 g, 4.3 mmol), DMSO (3 ml) and veratylamine (1.3 ml, 8.6 mmol) is heated at 80°–90° C. for 2 hours. The reaction mixture is cooled, and then is poured into water. A gummy oil formed which crystallized upon the addition of a few drops of ether. The solid is collected by filtration, washed with water and recrystallized from ethyl acetate to afford 1.0 g of 1-ethyl-N-(3,4-dimethoxy phenylmethyl)-1H-pyrazolo[3,4-b]quinolin-4-amine, m.p. 169°–171° C.

Example 8

A mixture of 1-ethyl-4-chloro-1H-pyrazolo[3,4-b]quinoline (1.0 g, 4.3 mmol), DMSO (3 ml) and 4-(aminomethyl)pyridine (0.92 ml, 9 mmol) is heated at 80°–90° C. overnight. The reaction mixture is poured into water (200 ml) NH4OH (1 ml), and the mixture is extracted with CH2Cl2 (3×100 ml). The CH2Cl2 layers are combined, dried over MgSO4 and evaporated. The residue is crystallized from ethyl acetate and recrystallized from ethyl acetate to afford 450 mg of 1-ethyl-N-(4-pyridinylmethyl)-1H-pyrazolo[3,4-b]quinolin-4-amine, m.p. 191°–192° C.

Example 9

(a) Hydrazine hydrate (32.5 ml, 0.67 mol) is added dropwise over 2–3 hours to a mixture of allyl cyanide (52 ml, 0.65 mol) and benzene (50 ml) while keeping the reaction temperature below 33° C. A solution of acetaldeyde (34.3 g, 0.78 mol) in benzene (100 ml) is then added dropwise to the reaction mixture and then the mixture is stirred at room temperature overnight. The benzene is evaporated and the residue is treated with butanol (250 ml) containing 1.5 g of dissolved sodium metal. The reaction mixture is refluxed for 5 hours, then is cooled to room temperature and is allowed to sit overnight. The butanol is evaporated in vacuo, and the residue is purified by Kuglerohr distillation at 0.4 mm Hg and 100°–115° C. to afford the product as an oil which crystallized on standing to produce 7.8 g of 5-amino-1-ethyl-3-methylpyrazole, m.p. 95°–96° C.

(b) A mixture of 5-amino-1-ethyl-3-methylpyrazole (7.5 g, 0.06 mol), 2-iodobenzoic acid (14.88 g, 0.06 mol), DMF (50 ml) Cu(OAc)2.H2O (0.5 g) and K2CO3 (8.3 g, 0.06 mol) is refluxed under a nitrogen atmosphere for 20 hours. The reaction mixture is cooled to room temperature and then is poured into ice water. The mixture is neutralized with acetic acid, and the resulting solid is collected by filtration, washed with water and dried to afford 7.1 g (48%) of N-(1-ethyl-3-methylpyrazol-5-yl)anthranilic acid.

(c) A mixture of N-(1-ethyl-3-methylpyrazol-5-yl) anthranilic acid (7.0 g, 28.57 mmol) and POCl3 (20 ml) is refluxed for 24 hours. The reaction mixture is cooled to room temperature and then is poured into ice water. The mixture is neutralized with concentrated NH4OH to a pH of about 8 and the resulting gum crystallized slowly to afford a solid which is collected by filtration, washed with water and dried to afford 6.7 g (95%) of 1-ethyl-3-methyl-4-chloro-1H-pyrazolo[3,4-b]quinolino.

(d) A mixture of 1-ethyl-3-methyl-4-chloro-1H-pyrazolo[3,4-b]quinoline (1.0 g, 4.3 mmol), DMSO (3 ml) and benzylamine (0.98 ml, 9 mmol) is heated at 80° C. overnight. The reaction mixture is poured into water (100 ml), then NH4OH (0.5 ml) is added. The mixture is extracted with CH2Cl2 (200 ml) and the CH2Cl2 is concentrated to about 20 ml, and then this solution is purified by column chromatography on silica gel, followed by high pressure liquid chromatography eluting with 20% ethyl acetate/hexane to afford the product as the free base. The free base is dissolved in CH2Cl2 (20 ml) and treated with ethereal HCl. The mixture is evaporated and the residue is crystallized from ether to afford 0.9 g of 1-ethyl-3-methyl-N-(phenylmethyl)-1H-pyrazolo[3,4-b]quinolin-4-amine.HCl, as an off white solid, m.p. 228°–231° C.

Example 10

A mixture of 1-ethyl-4-chloro-1H-pyrazolo[3,4-b]quinoline (1.0 g, 4.3 mmol), DMSO (3 ml) and 4-cyanobenzylamine (1.2 g, 9 mmol) is heated on a steam bath for 3 hours, then is allowed to sit at room temperature overnight. The reaction mixture is poured into water and an oil separated. The oil is extracted with hot 10% ethanol/ethyl acetate, washed with water, and the organic layer is dried and evaporated. The residue is crystallized from ether/ethyl acetate and then is purified by recrystallization from ethyl acetate/hexane, followed by column chromatography on silca gel eluting with ethyl acetate and finally crystallization of the residue thus obtained from ethyl acetate/hexane to afford 280 mg of 1-ethyl-N-(4-cyanophenylmethyl)-1H-pyrazolo[3,4-b]quinolin-4-amine, as yellow crystals, m.p. 233°–234° C.

Example 11

A mixture of 1-ethyl-4-chloro-1H-pyrazolo[3,4-b]quinoline (3.45 g, 0.015 mol), DMSO (12 ml) and 3-methoxybenzylamine (4.15 ml, 0.03 mol) is heated at 80°–90° C. for 3–4 hours. The reaction mixture is poured into water (300 ml) and then is extracted with ether (3×200 ml). The ether layers are combined, washed with water (200 ml), dried over MgSO4 and evaporated. The residue is purified by column chromatography on silca gel eluting with ethyl acetate to afford 5.6 g of the product as the free base.

The free base (1.0 g) is dissolved in ethanol and treated with ethanolic HCl. The ethanol is evaporated and ether and ethanol (2 ml) are added to the residue. The HCl salt is collected by filtration, washed with ether (25 ml) and dried in vacuo to afford 580 mg of 1-ethyl-N-(3-methoxyphenylmethyl)-1H-pyrazolo[3,4-b]quinolin-4-amine, as a white solid, m.p. 260°–263° C.

Example 12

(a) A mixture of 2-iodobenzoic acid (14.9 g, 0.06 mol), 5-amino-1,3-dimethylpyrazole (6.7 g, 0.06 mol), DMF (125 ml), Cu(OAc)2 (0,4 g) and K2CO3 (8.28 g, 0.06 mol) is refluxed overnight. The reaction mixture is poured into ice water (500 ml) and then is acidified with acetic acid to a pH of about 5. The solid that forms is collected by filtration, washed with water (100 ml) and dried. The solid is dissolved in hot CHCl3 (300 ml), filtered, dried over MgSO$_4$ and evaporated to about 20 ml. Hexane (50 ml) is added, and then the product is collected by filtration, washed with hexane (30 ml) and dried to afford 6.2 g of N-(1,3-dimethyl-pyrazol-5-yl)anthranilic acid, m.p. 210°–211° C.

(b) A mixture of N-(1,3-dimethyl-pyrazol-5-yl) anthranilic acid (7 g, 0.03 mol) and POCl3 (40 ml) is heated on a steam bath for 3 hours. The reaction mixture is then poured into ice water (600 ml) and then basified with NH4OH. The mixture is extracted with ether (3×200 ml), and the combined ether layers are dried over MgSO4 and evaporated to afford 7.0 g of 1,3-dimethyl-4-chloro-1H-pyrazolo[3,4-b] quinoline, m.p. 127°–129° C.

(c) A mixture of 1,3-dimethyl-4-chloro-1H-pyrazolo[3,4-b]quinoline (1.2 g, 0.005 mol), benzylamine (1.2 ml) and DMSO (3 ml) is heated at 80°–90° C. for 3–4 hours. The reaction mixture is cooled to room temperature and then is poured into water. The mixture is extracted with CH2Cl2 (3×50 ml) and then the CH2Cl2 layers are combined and evaporated. The residue is purified by column chromatography on silca gel eluting with ethyl acetate to afford the product which is crystallized from ether/hexane to afford 1.2 g of 1,3-dimethyl-N-(phenylmethyl)-1H-pyrazolo[3,4-b]quinolin-4-amine, as a yellow solid, m.p. 105° C.

Example 13

A mixture of 1-ethyl-N-(3-methoxyphenylmethyl)-1H-pyrazolo[3,4-b]quinolin-4-amine (3.8 g, 0.0114 mol) and pyridine hydrochloride (10 g) is heated at about 200° C. for 3 hours. The reaction mixture is cooled and then 10% NaOH (70 ml) is added. The mixture is washed with ether (2×30 ml) and then the aqueous layer is acidified with acetic acid to a pH of about 5. The solid which formed is collected by filtration and dried in vacuo to afford 2.5–3 g of 1-ethyl-N-(3-hydroxyphenylmethyl)-1H-pyrazolo[3,4-b]quinolin-4-amine, as an off-white solid, m.p. 273°–275° C.

Example 14

1-Ethyl-N-(3-hydroxyphenylmethyl)-1H-pyrazolo[3,4-b] quinolin-4-amine (350 mg) is dissolved in hot methanol (200 ml), and then 3 equivalents of methanesulfonic acid are added. The methanol is then evaporated to a volume of about 20 ml and one volume of ether is added. The solid that forms is collected by filtration, washed with ether, and dried to afford 340 mg of 1-ethyl-N-(3-hydroxyphenylmethyl)-1H-pyrazolo[3,4-b]quinolin-4-amine. 2 CH3SO3H, m.p.>240° C.

Example 15

(a) To a solution of 4-cyanophenol (5.95 g, 0.05 mol) in DMF (35 ml) at 0° C. is added 60% NaOH (2.2 g, 0.055 mol). The reaction mixture is stirred at 0° C. for 15 minutes, then at room temperature for 15 minutes and then N-(2-chloroethyl)morpholine (prepared from 11.16 g, 0.06 mol of the hydrochloride salt) is added, and the reaction mixture is stirred at room temperature for about two days. There is still a small amount of starting material present so the reaction mixture is heated on a steam bath for 4 hours. The reaction mixture is cooled to room temperature and then the solvent is removed. Ice water is added to the residue, and the solid which precipitats is collected by filtration and dried to afford 11.3 g (97%) of 4-[2-(4-morpholinyl)ethoxy]benzonitrile.

(b) A mixture of 4-[2-(4-morpholinyl)ethoxy]benzonitrile (0.93 g, 4 mmol), ethanol (100 ml), CHCl3 (4 ml) and PtO2 (100 mg) is hydrogenated at 45 psi on a Parr hydrogenator for 8 hours. Concentrated HCl (2–3 drops) is then added to the reaction mixture, and the hydrogenation is continued for another 10 hours. The catalyst is removed by filtration, the filter cake is washed with ethanol and then the filtrate is evaporated to dryness. The residue is dissolved in water and then is saturated with solid K2CO3. The mixture is extracted with CH2Cl2 and then the CH2Cl2 layer is dried over K2CO3 and evaporated to afford 0.75 g (79%) of 4-[2-(4-morpholinyl)ethoxy]phenylmethylamine.

(c) A mixture of 1-ethyl-4-chloro-1H-pyrazolo[3,4-b] quinoline (0.7 g, 3 mmol), 4-[2-(4-morpholinyl)ethoxy] phenylmethylamine (0.75 g, 3.2 mmol) and DMSO (3 ml) is heated on a steam bath for 8 hours. Additional 1-ethyl-4-chloro-1H-pyrazolo[3,4-b]quinoline (0.7 g, 3 mmol) is then added, and the reaction mixture is heated on a steam bath for another 4 hours. The reaction mixture is cooled to room temperature and then is poured into water. The mixture is extracted with CH2Cl2 (3×100 ml) and then CH2Cl2 layers are combined, dried over MgSO4 and evaporated to dryness. The residue is purified by column chromatography on silica gel eluting with CH2Cl2/methanol (95/5), followed by recrystallization from ethyl acetate, to afford 1.0 g of 1-ethyl-N-[4-[2-(4-morpholinyl)ethoxy]phenylmethyl]-1H-pyrazolo[3,4-b]quinolin-4-amine, as a yellow solid, m.p. 170°–172° C.

Example 16

A mixture of 1-ethyl-4-chloro-1H-pyrazolo[3,4-b] quinoline (1.0 g, 0.0043 mol), DMSO (3 ml) and 2-aminomethytfuran (0.8 ml, 0.009 mol) is heated at 90° for 3 hours. The reaction mixture is then partitioned between CH2Cl2 (50 ml) and water (50 ml). The aqueous layer is separated and then extracted with CH2Cl2 (25 ml), and then the CH2Cl2 layers are combined, washed with water dried over Na2SO4 and reduced to a volume of about 3–5 ml. The solution is passed through a silica gel column eluting with ethyl acetate to afford the product which is recrystallized from ether/CH2Cl2 to afford 430 mg of 1-ethyl-N-(2-furanylmethyl)-1H-pyrazolo[3,4-b]quinolin-4-amine, as a yellow solid, m.p. 156°–158° C.

Example 17

1-Ethyl-N-(2-furanylmethyl)-1H-pyrazolo[3,4-b] quinolin-4-amine (1.3 g) is dissolved in methanol (10 ml) and then is treated with methanesulfonic acid (1 ml). The methanol is evaporated, and the residue is crystallized from 2-propanol/ether and dried in vacuo to afford 1.12 g of 1-ethyl-N-(2-furanylmethyl)-1H-pyrazolo[3,4-b]quinolin-4-amine.CH3SO3H, m.p. 221°–222° C.

Example 18

(a) A mixture of 1-ethyl-N-(4-methoxyphenylmethyl)-1H-pyrazolo[3,4-b]quinolin-4-amine (7.0 g, 0.021 mol), boron tribromide (65 ml, 0.065 mol) and dichloroethane (250 ml) is stirred at room temperature for 1 hour and then is refluxed overnight. The reaction mixture is cooled and then is poured into ice water (100 ml). An aqueous solution of NaOH is added to the mixture, and then the mixture is sonicated. The layers are separated, and then the aqueous layer is washed with ether and then is acidified with acetic acid to pH of about 5–6. The precipitate that forms is collected by filtration to afford 5.6 g of the product as the free base. The free base (1.5 g) is then dissolved in hot methanol, and 3–5 equivalents of methanesulfonic acid (2 ml) are added. The salt is then crystallized from ether/isopropanol and then collected by filtration to afford 850 mg of 1-ethyl-N-(4-hydroxyphenylmethyl)-1H-pyrazolo[3,4-b]quinolin-4-amine.CH3SO3H, m.p. 280° C. (dec.).

(b) The free base (1.0 g) from example 18 (a) is I-5 recrystallized from hot ether/THF (200 ml) and dried at 80° C. in vacuo to afford 220 mg of 1-ethyl-N-(4-hydroxyphenylmethyl)-1H-pyrazolo[3,4-b]quinolin-4-amine, m.p. 279°–280° C.

Example 19

A mixture of 1-ethyl-4-chloro-1H-pyrazolo[3,4-b]-quinoline (1.0 g, 0.0043 mol), DMSO (1 ml) and 3-aminomethylpyridine (0.97 ml, 0.0093 mol) is heated at 90° C. for 4 hours. The reaction mixture is poured into water, and the solid that forms is collected by filtration and recrystallized from ether/CH2Cl2/hexane to afford the product as the free base. The free base is dissolved in methanol (100 ml) and then is treated with methanesulfonic acid (1 ml). The methanol is evaporated, and then the residue is crystallized from 2-propanol/ether. The product is collected by filtration, washed with ether and dried in vacuo to afford 1.0 g of 1-ethyl-N-(3-pyridinylmethyl)-1H-pyrazolo[3,4-b]quinolin-4-amine.2CH3SO3H, m.p. 282°–284° C.

Example 20

A mixture of 1-ethyl-4-chloro-1H-pyrazolo[3,4-b]quinoline (1.0 g, 0.0043 mol), DMSO (3 ml) and N-methylbenzylamine (1 ml, 0.009 mol) is heated at 90° C. for four hours. The reaction mixture is partitioned between CH2Cl2/water and then the CH2Cl2 layer is separated and evaporated. The residue is purified by column chromatography on silica gel eluting with ethyl acetate to afford 0.9 g of the product as the free base. The free base is dissolved in methanol (100 ml) and then is treated with methanesulfonic acid (1 ml). The methanol is evaporated, and the residue is crystallized from 2-propanol/ether. The product is collected by filtration, washed with ether and dried in vacuo to afford 0.6 g of 1-ethyl-N-(methyl)-N-(phenylmethyl)-1H-pyrazolo[3,4-b]quinolin-4-amine.CH3SO3H, m.p. 175°–177° C.

Example 21

A mixture of 1-ethyl-4-chloro-1H-pyrazolo[3,4-b]quinoline (1.0 g, 0.0043 mol), DMSO (3 ml) and 2-aminomethylpyridine (0.9 ml, 0.0086 mol) is heated at 110° C. overnight. The reaction mixture is cooled and then is poured into water. The mixture is extracted with CH2Cl2, and then the CH2Cl2 layer is evaporated. The residue is purified by column chromatography on silica gel eluting with 20% hexane/ethyl acetate to afford the product as the free base. The free base is then dissolved in methanol and is treated with methanesulfonic acid. The methanol is evaporated and the residue is recrystallized from 2-propanol/ether and dried in vacuo to afford 1.0 g of 1-ethyl-N-(2-pyridinylmethyl)-1H-pyrazolo[3,4-b]quinolin-4-amine.2CH3SO3H, as a yellow solid m.p. 259°–260° C.

Example 22

A mixture of 1-ethyl-4-chloro-1H-pyrazolo[3,4-b]quinoline (1.0 g, 0.0043 mol), DMSO (3 ml) and 1-aminoindane (1 g) is heated at 110° C. for 16 hours. The reaction mixture is cooled, and then is poured into water (100 ml). The solid that forms is collected by filtration and dried to afford the product as the free base. The free base is dissolved in methanol and then is treated with methanesulfonic acid. The methanol is evaporated, and the residue is crystallized from hot methanol/2-propanol and then is recrystallized from hot methanol/2-propanol to afford 717 mg of 1-ethyl-N-(1-indanyl)-1H-pyrazolo[3,4-b]quinolin-4-amine.CH3SO3H, m.p. 233°–235° C.

Example 23

(a) A mixture of 2-bromo-5-methoxybenzoic acid (141.5 g, 0.61 mol), 5-amino-1-ethylpyrazole (68 g, 0.61 mol), K2CO3 (84.2 g, 0.61 mol), DMF (500 ml) and Cu(OAc)$_2$ (3 g) is refluxed for about 2 days. The reaction mixture is cooled and then is poured into water (1500 ml). The mixture is acidified with acetic acid, and the resulting solid is collected by filtration and dried to afford 110 g of N-(1-ethylpyrazol-5-yl)-5-methoxyanthranilic acid.

(b) A mixture of N-(1-ethylpyrazol-5-yl)-5-methoxyanthranilic acid (110 g, 0.421 mol) and POCl3 (300 ml) is refluxed overnight and then is allowed to stand at room temperature for about 3 days. The reaction mixture is poured into ice water and then is basified with NH4OH. The solid that forms is collected by filtration, washed with water and air dried to afford 100.5 g of 1-ethyl-4-chloro-6-methoxy-1H-pyrazolo[3,4-b]quinoline.

(c) A mixture of 1-ethyl-4-chloro-6-methoxy-1H-pyrazolo[3,4-b]quinoline (2.0 g, 7.66 mmol), DMSO (6 ml) and 4-methoxybenzylamine (2.2 ml, 16.9 mmol) is heated at 110° C. overnight. The reaction mixture is cooled, and then is poured into water. The mixture is extracted with ethyl acetate and then the ethyl acetate layer is dried over MgSO4, filtered and evaporated. The residue is purified by column chromatography on silica gel eluting with ethyl acetate to afford 2.0 g of the product as the free base. The free base (1.0 g) is suspended in methanol and then is treated with methanesulfonic acid. The salt that precipitats is collected by filtration, recrystallized from methanol and dried in vacuo to afford 740 mg of 1-ethyl-6-methoxy-N-(4-methoxyphenyl methyl)-1H-pyrazolo[3,4-b]quinolin-4-amine.CH3SO3H, as a yellow solid, m.p. 263°–265° C.

Example 24

A mixture of 1-ethyl-6-methoxy-N-(4-methoxyphenylmethyl)-1H-pyrazolo[3,4-b]quinolin-4-amine (1.0 g, 2.76 mmol), boron tribromide (6 ml, 6 mmol) and 1,2-ethylenedichloride (30 ml) is stirred at room temperature overnight. The reaction mixture is poured into water and then is basified with NaOH. The layers are separated, and then the aqueous layer is acidified with acetic acid. The precipitate that forms is collected by filtration, washed with water and dried to afford the product as the free base. The free base is taken up in methanol and treated with methanesulfonic acid. The methanol is evaporated and the solid residue is recrystallized from 2-propanel/methanol/ether and dried in vacuo to afford 350 mg of 1-ethyl-6-hydroxy-N-(4-hydroxyphenyl methyl)-1H-pyrazolo[3,4-b]quinolin-4-amine.CH3SO3H.

With a procedure similar to that described in Example 12(c), but substituting an appropriate compound of the Formula III for benzylamine, it is contemplated that the compounds of the Formula I illustrated in Examples 25–30 can be prepared.

Example 25

1,3-Dimethyl-N-[S-(−)-1-(phenyl)ethyl]-1H-pyrazolo[3,4-b]quinolin-4-amine.

Example 26

1,3-Dimethyl-N-(4-chlorophenylmethyl)-1H-pyrazolo[3,4-b]quinolin-4-amine.

Example 27

1,3-Dimethyl-N-(3-methylphenylmethyl)-1H-pyrazolo[3,4-b]quinolin-4-amine.

Example 28

1,3-Dimethyl-N-(2-thienylmethyl)-1H-pyrazolo[3,4-b]quinolin-4-amine.

Example 29

1,3-Dimethyl-N-(2-pyrazinylmethyl)-1H-pyrazolo[3,4-b]quinolin-4-amine.

Example 30

1,3-Dimethyl-N-(5-isoxazolylmethyl)-1H-pyrazolo[3,4-b]quinolin-4amine.

Example 31

With procedures similar to those described in Examples 5(c)–5(e), but substituting 2-bromo-4-methylbenzoic acid for 2-iodo-4-methoxybenzoic acid in Example 5(c), it is contemplated that there can be prepared:

(a) N-(1-Ethylpyrazol-5-yl)-4-methylanthranilic acid.

(b) 1-Ethyl-4-chloro-7-methyl-1H-pyrazolo[3,4-b]quinoline.

(c) 1-Ethyl-7-methyl-N-phenylmethyl)-1H-pyrazolo[3,4-b]quinolin-4amine.

Example 32

With procedures similar to those described in Examples 5(c)–5(e), but substituting 2,6-dibromobenzoic acid for 2-iodo-4-methoxybenzoic acid in Example 5(c), it is contemplated that there can be prepared:
N-(1-Ethylpyrazol-5-yl)-5-bromoanthranilic acid.
1-Ethyl-4-chloro-6-bromo-1H-pyrazolo[3,4-b]quinoline.
1-Ethyl-6-bromo-N-(phenylmethyl)-1H-pyrazolo[3,4-b]quinolin-4amine.

The compounds of this invention can be formulated with pharmaceutically acceptable carriers into unit dosage forms in a conventional manner so that the patient in need of therapy for precancerous lesions can periodically (e.g., once or more per day) take a compound according to the method of this invention. The exact initial dose of the compounds of this invention can be determined with reasonable experimentation. It is believed that an initial intravenous dose will range from 0.46 μg to 40 mg for an average adult, and a daily dose for such an adult will range from 2 mg to 160 mg.

It will be understood that various changes and modifications can be made in the details of procedure, formulation and use without departing from the spirit of the invention, especially as defined in the following claims.

We claim:

1. A method for inhibiting the growth of neoplastic cells comprising exposing the cells sensitive to such a compound to a growth inhibiting effective amount of a compound of Formula I:

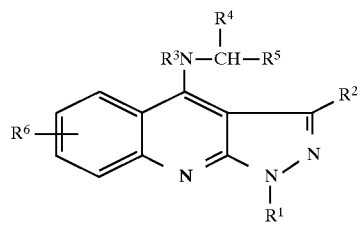

wherein:

$R_1$ is lower-alkyl;

$R_2$ is hydrogen, or lower-alkyl;

$R_3$ is hydrogen, or lower-alkyl;

$R_4$ is hydrogen, or lower-alkyl;

$R_5$ is phenyl (or phenyl substituted by from one to three, the same or different, substituents selected from the group consisting of lower-alkoxy, cyano, hydroxy, 4-morpholinylloweralkoxy, lower-alkyl, and halogen), phenyl-lower-alkyl, pyridinyl, furanyl, isoxazolyl, thienyl, oxazolyl, thiazolyl, pyridazinyl, pyrazinyl, and pyrirmidinyl; or $R_4$ and $R_5$ together with the CH group to which they are bonded form an indanyl ring; and $R_6$ is from one to three, the same or different, substituents selected from the group consisting of hydrogen, lower-alkoxy, hydroxy, lower-alkyl, and halogen; or a pharmaceutically acceptable acid-addition salt and/or hydrate thereof, or, where applicable, enantiomer or a racemic mixture.

2. The method of claim 1 wherein $R_4$ is hydrogen;

$R_5$ is phenyl (or phenyl substituted by from one to two, the same or different, substituents selected from the group consisting of lower-alkoxy, cyano, hydroxy, and 4-morpholinyllower-alkoxy), phenyl-lower-alkyl, pyridinyl, or furanyl; or $R_4$ and $R_5$ together with the CH group to which they are bonded form an indanyl ring; and $R_6$ is one substituent selected from the group consisting of hydrogen, lower-alkoxy, and hydroxy.

3. The method of claim 2 wherein $R_1$ is selected from the group consisting of methyl, ethyl or isopropyl;

$R_2$ is selected from the group consisting of hydrogen or methyl;

$R_3$ is selected from the group consisting of hydrogen or methyl;

$R_4$ is hydrogen;

$R_5$ is phenyl (or phenyl substituted by from one to two, the same or different, substituents selected from the group consisting of lower-alkoxy, cyano, hydroxy, and 4-morpholinyllower-alkoxy), phenyl-lower-alkyl, pyridinyl, or furanyl; or $R_4$ and $R_5$ together with the CH group to which they are bonded form an indanyl ring; and $R_6$ is one substituent selected from the group consisting of hydrogen, methoxy, and hydroxy.

4. The method of claim 3 wherein $R_5$ is phenyl (or phenyl substituted by from one to two, the same or different, substituents selected from the group consisting of methoxy, cyano, hydroxy, and 2-(4-morpholinyl)ethoxy), benzyl, 2-, 3-, 4-pyridinyl, or 2-furanyl; or $R_4$ and $R_5$ together with the CH group to which they are bonded form an indanyl ring.

5. The method of claim 1 wherein the compound is selected from the group consisting of: N-(phenylmethyl)-1-ethyl-1H-pyrazolo[3,4-b]quinolin-4-amine; N-(2-furanylmethyl)-1-ethyl-1H-pyrazolo [3,4-b]quinolin-4-amine; and N-(4-methoxyphenylmethyl)-1-ethyl-6-methoxy-1H-pyrazolo [3,4-b]quinolin-4-amine.

6. A method of treating a mammal having precancerous lesions sensitive to such a compound comprising administering to said mammal a pharmacologically effective amount of a compound of Formula I:

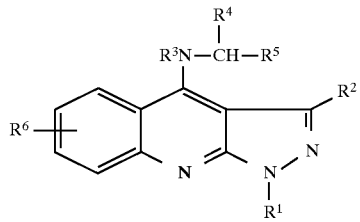

wherein:

$R_1$ is lower-alkyl;

$R_2$ is hydrogen, or lower-alkyl;

$R_3$ is hydrogen, or lower-alkyl;

$R_4$ is hydrogen, or lower-alkyl;

$R_5$ is phenyl (or phenyl substituted by from one to three, the same or different, substituents selected from the group consisting of lower-alkoxy, cyano, hydroxy, 4-morpholinylloweralkoxy, lower-alkyl, and halogen), phenyl-lower-alkyl, pyridinyl, furanyl, isoxazolyl, thienyl, oxazolyl, thiazolyl, pyridazinyl, pyrazinyl, and pyrimidinyl; or $R_4$ and $R_5$ together with the CH group to which they are bonded form an indanyl ring; and $R_6$ is from one to three, the same or different, substituents selected from the group consisting of hydrogen, lower-alkoxy, hydroxy, lower-alkyl, and halogen; or a pharmaceutically acceptable acid-addition salt and/or hydrate thereof, or, where applicable, enantiomer or a racemic mixture.

7. The method of claim 6 wherein $R_4$ is hydrogen;

$R_5$ is phenyl (or phenyl substituted by from one to two, the same or different, substituents selected from the group consisting of lower-alkoxy, cyano, hydroxy, and 4-morpholinyllower-alkoxy), phenyl-lower-alkyl, pyridinyl, or furanyl; or $R_4$ and $R_5$ together with the CH group to which they are bonded form an indanyl ring; and $R_6$ is one substituent selected from the group consisting of hydrogen, lower-alkoxy, and hydroxy.

8. The method of claim 7 wherein $R_1$ is selected from the group consisting of methyl, ethyl or isopropyl;

$R_2$ is selected from the group consisting of hydrogen or methyl;

$R_3$ is selected from the group consisting of hydrogen or methyl;

$R_4$ is hydrogen;

$R_5$ is phenyl (or phenyl substituted by from one to two, the same or different, substituents selected from the group consisting of lower-alkoxy, cyano, hydroxy, and 4-morpholinyllower-alkoxy), phenyl-lower-alkyl, pyridinyl, or furanyl; or $R_4$ and $R_5$ together with the CH group to which they are bonded form an indanyl ring; and $R_6$ is one substituent selected from the group consisting of hydrogen, methoxy, and hydroxy.

9. The method of claim 8 wherein $R_5$ is phenyl (or phenyl substituted by from one to two, the same or different, substituents selected from the group consisting of methoxy, cyano, hydroxy, and 2-(4-morpholinyl)ethoxy), benzyl, 2-, 3-, 4-pyridinyl, or 2-furanyl; or $R_4$ and $R_5$ together with the CH group to which they are bonded form an indanyl ring.

10. The method of claim 6 wherein the compound is selected from the group consisting of: N-(phenylmethyl)-1-ethyl-1H-pyrazolo[3,4-b]quinolin-4-amine; N-(2-furanylmethyl)-1-ethyl-1H-pyrazolo[3,4-b]quinolin-4-amine; and N-(4-methoxyphenylmethyl)-1-ethyl-6-methoxy-1H-pyrazolo [3,4-b]quinolin-4-amine.

11. A method for regulating apoptosis in human cells comprising exposing said cells sensitive to such a compound to an effective amount of a compound of the formula:

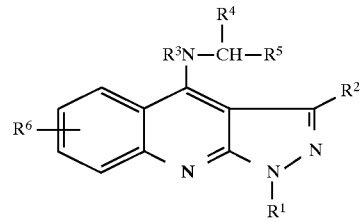

wherein:

$R_1$ is lower-alkyl;

$R_2$ is hydrogen, or lower-alkyl;

$R_3$ is hydrogen, or lower-alkyl;

$R_4$ is hydrogen, or lower-alkyl;

$R_5$ is phenyl (or phenyl substituted by from one to three, the same or different, substituents selected from the group consisting of lower-alkoxy, cyano, hydroxy, 4-morpholinylloweralkoxy, lower-alkyl, and halogen), phenyl-lower-alkyl, pyridinyl, furanyl, isoxazolyl, thienyl, oxazolyl, thiazolyl, pyridazinyl, pyrazinyl, and pyrimidinyl; or $R_4$ and $R_5$ together with the CH group to which they are bonded form an indanyl ring; and $R_6$ is from one to three, the same or different, substituents selected from the group consisting of hydrogen, lower-alkoxy, hydroxy, lower-alkyl, and halogen; or a pharmaceutically acceptable acid-addition salt and/or hydrate thereof, or, where applicable, enantiomer or a racemic mixture.

12. The method of claim 11 wherein $R_4$ is hydrogen;

$R_5$ is phenyl (or phenyl substituted by from one to two, the same or different, substituents selected from the group consisting of lower-alkoxy, cyano, hydroxy, and 4-morpholinyllower-alkoxy), phenyl-lower-alkyl, pyridinyl, or furanyl; or $R_4$ and $R_5$ together with the CH group to which they are bonded form an indanyl ring; and $R_6$ is one substituent selected from the group consisting of hydrogen, lower-alkoxy, and hydroxy.

13. The method of claim 12 wherein $R_1$ is selected from the group consisting of methyl, ethyl or isopropyl;

$R_2$ is selected from the group consisting of hydrogen or methyl;

$R_3$ is selected from the group consisting of hydrogen or methyl;

$R_4$ is hydrogen;

$R_5$ is phenyl (or phenyl substituted by from one to two, the same or different, substituents selected from the group consisting of lower-alkoxy, cyano, hydroxy, and 4-morpholinyllower-alkoxy), phenyl-lower-alkyl, pyridinyl, or furanyl; or $R_4$ and $R_5$ together with the CH group to which they are bonded form an indanyl ring; and $R_6$ is one substituent selected from the group consisting of hydrogen, methoxy, and hydroxy.

14. The method of claim 13 wherein $R_5$ is phenyl (or phenyl substituted by from one to two, the same or different, substituents selected from the group consisting of methoxy, cyano, hydroxy, and 2-(4-morpholinyl)ethoxy), benzyl, 2-, 3-, 4-pyridinyl, or 2-furanyl; or $R_4$ and $R_5$ together with the CH group to which they are bonded form an indanyl ring.

15. The method of claim 14 wherein the compound is selected from the group consisting of: N-(phenylmethyl)-1-ethyl-1H-pyrazolo[3,4-b]quinolin-4-amine; N-(2-furanylmethyl)-1-ethyl-1H-pyrazolo[3,4-b]quinolin-4-amine; and N-(4-methoxyphenylmethyl)-1-ethyl-6-methoxy-1H-pyrazolo [3,4-b]quinolin-4-amine.

* * * * *